United States Patent [19]

Butler

[11] 3,996,513
[45] Dec. 7, 1976

[54] DIFFERENTIAL MICROAMPERE CURRENT SENSOR

[76] Inventor: Fred C. Butler, 332 Macomber Rd., Chehalis, Wash. 98532

[22] Filed: Apr. 24, 1975

[21] Appl. No.: 571,237

[52] U.S. Cl. .................... 324/62; 324/51; 324/127; 336/84; 336/175
[51] Int. Cl.² ............... H01F 15/02; G01R 27/02; G01R 31/02
[58] Field of Search .............. 324/62, 51, 127; 336/90, 82, 83, 84, 174, 175, 212

[56] References Cited
UNITED STATES PATENTS

| | | | |
|---|---|---|---|
| 3,024,434 | 3/1962 | Carson, Jr. | 336/96 |
| 3,183,406 | 5/1965 | Neydli | 317/99 |
| 3,356,939 | 12/1967 | Stevenson | 324/51 |
| 3,665,356 | 5/1972 | Douglas et al. | 336/73 |
| 3,683,302 | 8/1972 | Butler et al. | 336/83 |
| 3,885,213 | 5/1975 | Rioux et al. | 324/127 |
| 3,891,895 | 6/1975 | Wittlinger | 317/18 D |

Primary Examiner—Robert Segal
Assistant Examiner—Vincent J. Sunderdick
Attorney, Agent, or Firm—Allen A. Dicke, Jr.

[57] ABSTRACT

Ultrasensitive current sensor detects unbalanced current in two or more AC load conductors passing therethrough. Coaxial conductors are surrounded by search sensor coil, the signal from which is amplified.

14 Claims, 3 Drawing Figures

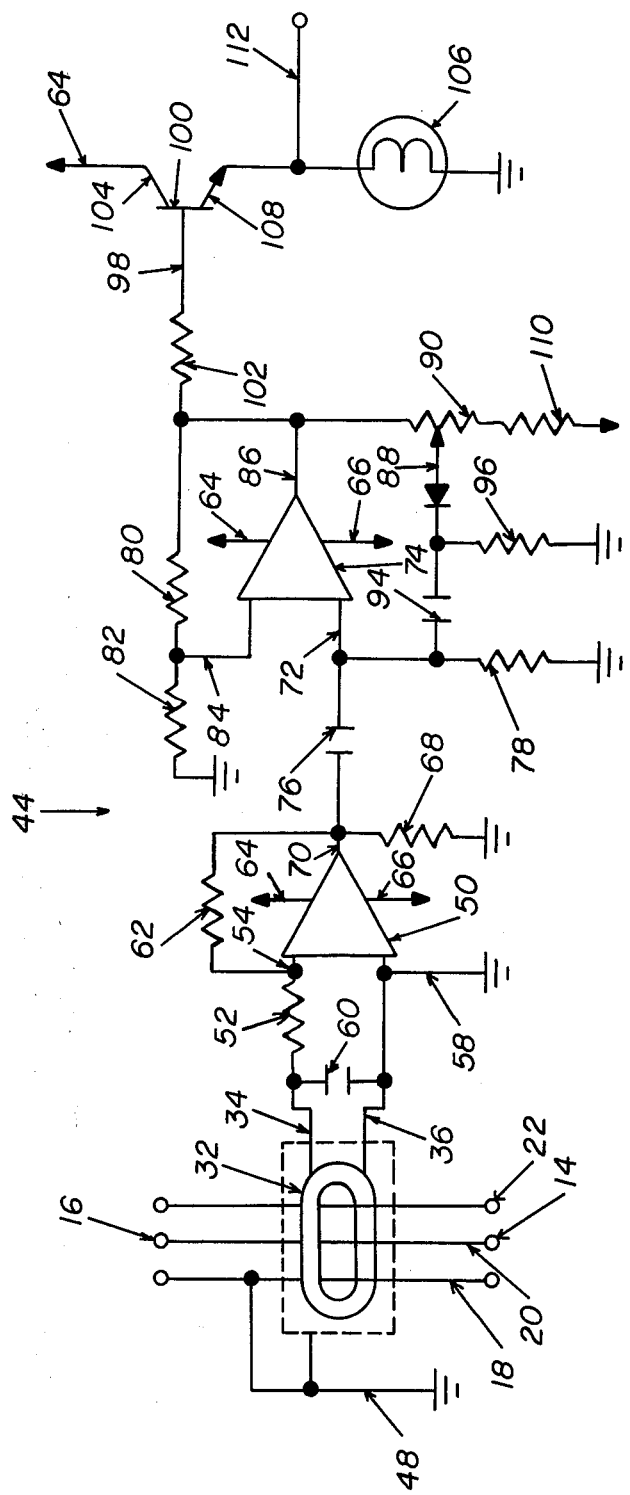

DIFFERENTIAL MICROAMPERE CURRENT SENSOR

BACKGROUND

This invention is directed to a current sensor capable of sensing unbalanced current in AC load conductors together with a detector circuit energized by the sensor so as to form a ground fault sensing and signaling apparatus.

Ordinary residential and industrial electric circuits are routinely protected against excessive current loads so that the circuit is interrupted before there is damage to the wiring or to the structure in which they are installed; however such circuits are usually unprotected against high resistance leakage paths which have a sufficient resistance to limit the current to a value less than that required to actuate the excess current circuit protection equipment.

Particularly in medical equipment and also wherever a ground path through the person is possible, there are health hazards from such shock. The hazards and other criteria are discussed in greater detail in my prior U.S. Pat. No. 3,683,302, the entire disclosure of which is incorporated herein by this reference.

Particularly in hospital situations with equipment containing electrical devices being connected to a patient is the hazard acute. When the patient's skin resistance is broken, the internal body resistance through the heart muscle is very low so that very low currents can cause severe physiological reactions.

Differential current transformers of the general type as this invention are largely used in commercial ground fault circuit interrupter equipment as ground fault sensors; however due to apparent limitations in the art, these sensor devices are limited to milliampere current resolution, thus unable to detect microampere current levels. The aforementioned limitations are considered to be due to the power conductor geometry problems which result in excessive leakage flux within the sensor means and inadequate shielding from external electrostatic and magnetic fields, either of which may cause an error signal to appear at the sensor output terminals. This invention provides a means for overcoming the limitations of other known current sensors by the novel arrangement of the power-carrying conductors, improved shielding means, and improved design of the detector coil including impedance matching.

SUMMARY

In order to aid in the understanding of this invention, it can be stated in essentially summary form that it is desired to a differential current sensor having mechanically fixed power-carrying conductors in a particular geometric relationship with a sensor coil therearound for connection to detector signaling and/or control circuitry.

It is thus an object of this invention to provide an ultrasensitive current sensor that can detect an unbalanced current condition of two or more AC load conductors carrying loads up to 25 amperes or more, even when the imbalance is 10 microamperes or less, and to produce a signal output from the sensor search coil suitable for amplification by electronic means. It is a further object of this invention to provide such a sensor that is substantially immune to interference, such as stray magnetic fields, electrostatic noise, and line carrier noises. It is a further object of this invention to provide a microampere current sensor that is economical to build and simple to utilize.

Other objects and advantages of this invention will become apparent from the study of the following portion of the specification, the claims, and the attached drawings.

BRIEF DESCRIPTION OF THE DRAWINGS

FIG. 3 is an electrical schematic circuit of the detector of this invention.

DESCRIPTION

Figure 1:
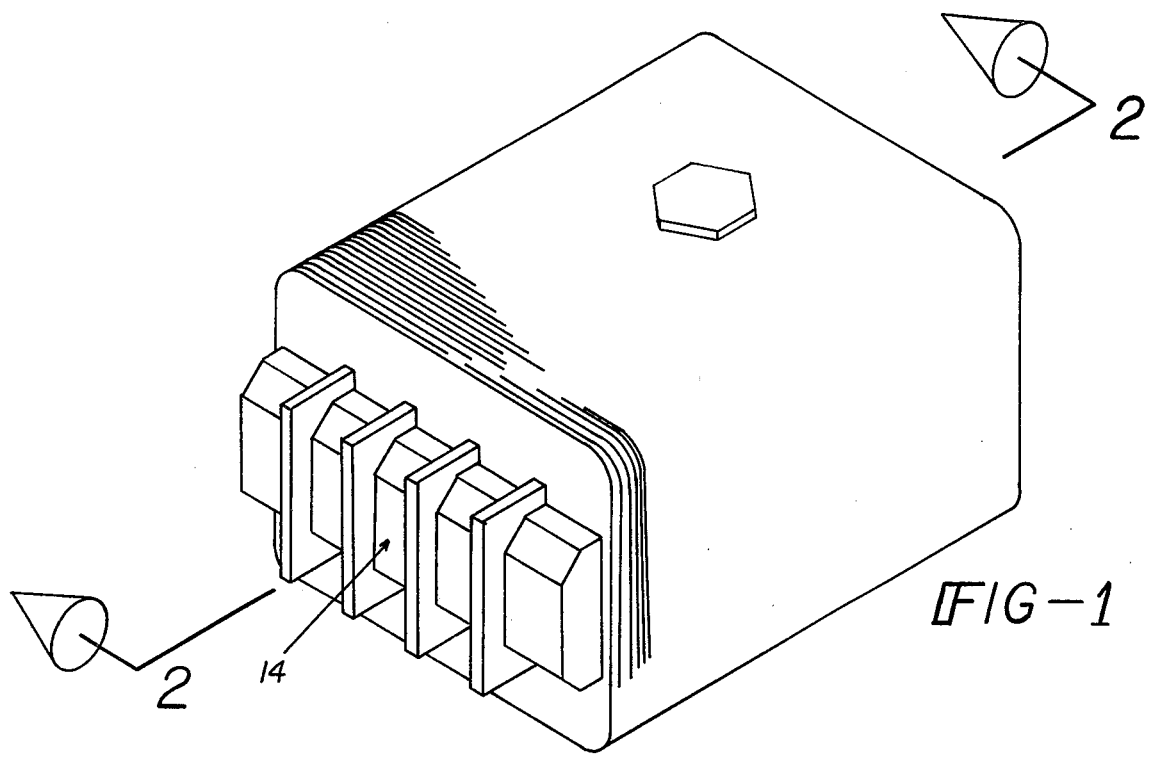
FIG. 1 is an isometric view of the differential current detector structure in accordance with this invention.
Figure 2:
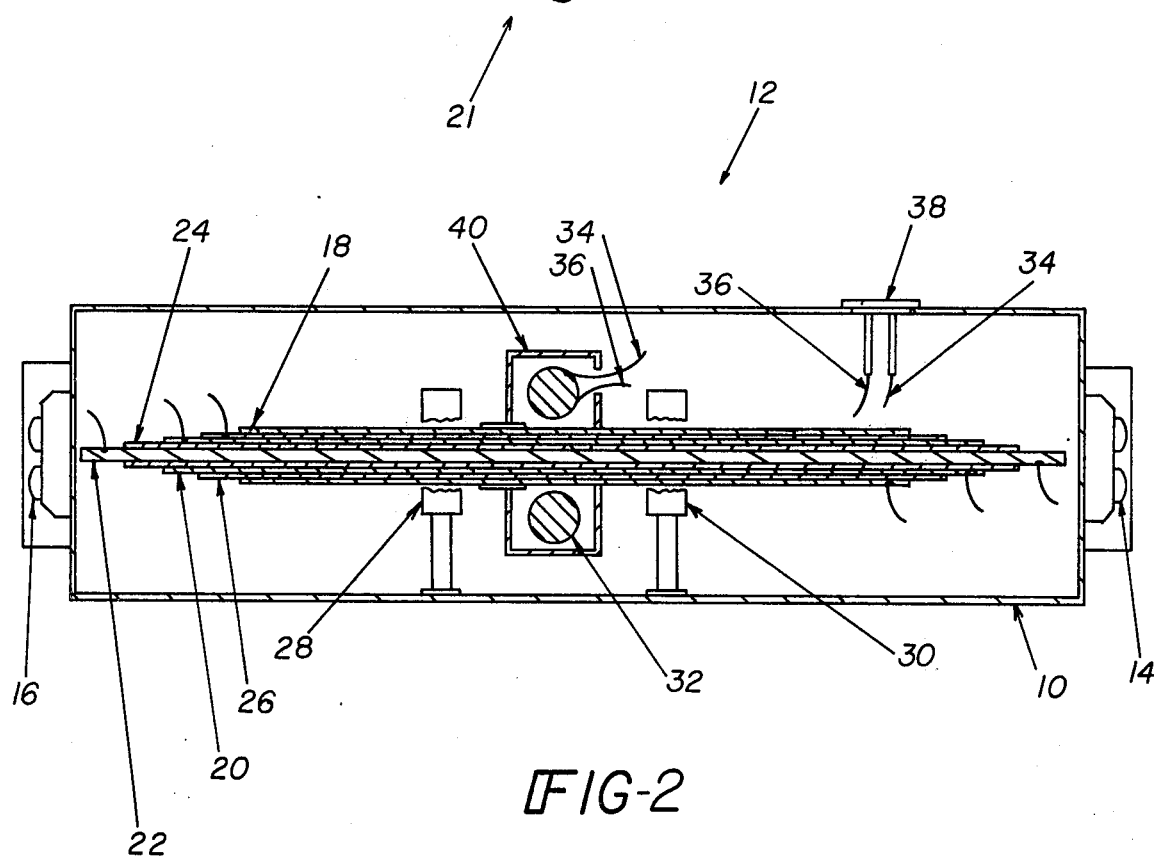
FIG. 2 is a section taken generally along the line 2—2 of FIG. 1.

FIG. 1 illustrates housing 10 of differential current sensor 12. Terminal contacts, such as contacts 14 and 16 are positioned in each end of the housing. The housing contains the concentric conductors and the sensor coil. As is seen in FIG. 2, concentric conductors 18, 20, and 22 extend through the housing from adjacent each end and on an axis. Concentric conductors 18, 20, and 22 are separated by insulator layers 24 and 26 so that they are electrically isolated from each other. Each of the conductors is firmly positioned in place by virtue of the insulation therebetween to retain them in the concentric construction. The outer conductor 18 is secured in insulated mounting posts 28 and 30 so that the entire conductor structure is held rigid in its housing. As is seen in FIG. 3, the outer conductor 18 is a ground conductor grounded to both the housing 10 and to an earth ground. It serves as a shield. Each of the conductors 18, 20, and 22 is preferably made of rigid brass for the tubular conductors. Each end of each of the conductors 18, 20, and 22 is connected to an individual set of contacts 14 and 16 so that, when the sensor is connected into an electric circuit, all of the circuit current passes therethrough. The geometric relationship of the conductors produces a magnetic balance or zero at a node point when current is balanced. Firmly fixed parallel conductors can be employed, but much careful adjustment is necessary to obtain a magnetic zero at the selected node point.

Sensor coil 32 is the basic detector of differential current and is sometimes called a "search coil." Sensor coil 32 has a ferromagnetic toroid with a multi-turn secondary wound thereabout. Sensor output leads 34 and 36 are connected to connector plug 38 on housing 10.

The sensor of search coil 32 monitors the current that flows through the triaxially disposed conductors 18, 20, and 22 passing through the window of the toroid 32 and will detect any imbalance thereof. As long as the current flowing in any one of the conductors to the load returns to the source through either or both the other conductors, there will be no flux generated within the search coil 32; however whenever a portion of that load current bypasses the search coil in returning to the source (for example, one microampere), flux lines will be generated within the coil, hence a signal will appear at its output which will be in direct proportion to the bypass or "fault" current.

For best performance, conductors 18, 20, and 22 must be concentrically disposed and uniform in cross-sectional dimensions throughout the length of the assembly. Also, the search coil must be centrally positioned for optimum response to internal flux lines.

Shielding is also a prime factor for low level current detection. Therefore, both ferromagnetic shielding and electrostatic shielding of the Faraday relativistic type are necessary. This shielding is provided by coil housing 40 which embraces sensor coil 32. Coil housing 40 is of high permeability ferromagnetic shielding material for this purpose.

FIG. 3 is a schematic which shows the relationship between the differential sensor 12 and fault current level detector circuit 44 in a typical microampere detector apparatus as applied to a single phase 120 volt electrical distribution circuit. Electrical power conductors 18, 20, and 22 pass through the window 46 of differential transformer 32, thereby constituting single turn primaries. Conductor 18 is the "ground" conductor, usually represented as the green wire of an electrical distribution circuit, and is connected to earth ground 48 or "house" ground near the main circuit breaker, and is not intended to carry power to the loads. Lines 20 and 22 represent the load-carrying conductors, one of which may also be connected to earth ground. In the case of hospital patient care areas, it is a common practice to "float" the power system, in which neither conductor 20 nor 22 would be grounded (via an isolation transformer). The shield structure in FIG. 3 is housing 10 which provides both magnetic shielding and electrostatic shielding for transformer 32 by relating the shield 10 to conductor 18 via interconnect 48. Lines 34 and 36 are the output leads from the multi-turn secondary of transformer 32, which is fed to amplifier 50 via resistor 52 to the inverting input 54. The non-inverting input 56 and the return leg 36 of coil 32 are grounded to the chassis at 58. Capacitor 60 serves (with the inductance of coil 32) as a filter network for transient suppression. The network may be resonated at power line frequency for improved performance. Amplifier 50 is preferably an operational amplifier, usually with integrated circuit components. Resistors 62 and 52 are selected to establish the predetermined gain factor with stability a prime factor. Lines 64 and 66 are connected to the positive and negative DC power supply sources necessary for proper powering of the operational amplifier. Resistor 68 is a load resistor for amplifier 50 attached to output line 70. The output signal in line 70 is fed to the non-inverting input 72 of amplifier 74 via DC blocking capacitor 76 and across resistor 78. Gain of amplifier 74 is determined by the ratio of resistors 80 and 82, the junction of which is common with the inverting input 84. Whenever the amplified fault signal at output terminal 86 of amplifier 74 reaches sufficient magnitude, the bias set at arm 88 of potentiometer 90 is overcome, and a voltage will appear at the non-inverting input 72 via diode 92 and network 78, 94, and 96, at which time the amplifier 74 output at 86 will suddenly swing to a positive voltage near the potential of 64. This is called "latch-up". Due to the capacitive coupling of the feedback voltage via capacitor 94 and the time constants of components 94, 96, and 78, the circuit will tend to oscillate or switch on and off, thereby providing a pulsating signal at the base 98 of transistor 100 via bias resistor 102. Since the collector 104 of transistor 100 is directly tied to the positive supply bus 64 and the load lamp 106 is connected between emitter 108 and ground 58 in an "emitter follower" configuration, the transistor will go into saturation, thus allowing the lamp to glow at full brightness in a pulsating fashion, as long as sufficient fault signal is present at the transformer 32 output 34.

Since the potentiometer 90 is related to a regulated DC bus 66 via limit resistor 110, the system can be calibrated to signal alarm at a predetermined fault current level; e.g., 5 or 10 microamperes. The output signal at line 112 from transistor 100 emitter 108 can be further processed to operate circuit breakers, relays, etc., with or without time delay.

By means of the double shielding, both by the shielding provided by ferromagnetic coil housing 40 and the shielding provided by ferromagnetic housing 10, the sensing coil is shielded from stray fields. Furthermore, the outer concentric conductor 18 is the ground conductor to shield against electrical fields. All three conductors are firmly located with respect to each other and with respect to the coil 32 by means of housing 40 being mounted on conductor 18. Furthermore, coil 32 is potted in housing 40 to prevent relative motion. Each of these related structures provides a non-variable relationship between the conductors and the search coil 32 so that faults of much smaller current value can be detected. When the imbalance is as litle as 10 microamperes or less, in load currents up to 25 amperes, the imbalance is detected. This provides especially valuable protection for patient care wards, including intensive care units and operating rooms to detect the small ground fault currents which can cause a safety hazard to the patient. The sensor and the related detection equipment achieve this goal of very much increased activity. The use of the sensor and detector in patient protection is an example of their use. They are separately and jointly useful in any place where ground faults or differential currents are to be detected.

This invention having been described in its preferred embodiment, it is clear that it is susceptible to numerous modifications and embodiments within the ability of those skilled in the art and without the exercise of the inventive faculty. Accordingly, the scope of this invention is defined by the scope of the following claims.

What is claimed is:

1. A sensor for a differential current detector, said sensor comprising first, second, and third mutually insulated conductors, said first, second, and third conductors being rigidly fixed with respect to each other within said sensor;
    a multi-turn sensor coil positioned around said conductors, said first, second, and third mutually insulated conductors each being rigidly fixed with respect to said sensor coil so that differential currents between said first, second, and third conductors are detected by said sensor coil; and
    a magnetic shielding housing positioned around said sensor coil and the portion of said first, second, and third conductors within said sensor coil to substantially shield said sensor coil from other magnetic fields.

2. The sensor of claim 1 wherein said shield is rigidly mounted with respect to said conductors.

3. The sensor of claim 1 wherein said shield around said sensor coil is a first shield and a second shield is mounted around said first, second, and third conductors and around said first shield to further shield said sensor coil from external magnetic fields.

4. The sensor of claim 1 wherein said first conductor is an inner conductor having an axis and said second and third conductors are tubular and are coaxially mounted with insulation between said first and second conductors and between said second and third conductors to provide a rigid, unitary conductor structure.

5. The sensor of claim 4 wherein said shield is mounted on said third conductor.

6. The sensor of claim 5 wherein said shield around said sensor coil is a first shield and a second shield is mounted around said conductors and around said first shield to further shield said sensor coil from external magnetic fields.

7. The sensor of claim 6 wherein said third conductor is a shielding conductor and is electrically connected to said first shield and to said second shield.

8. The sensor of claim 1 further including an electronic detector circuit having an output signal when said sensor coil detects unbalanced current between said conductors in excess of a predetermined value.

9. The detector of claim 8 wherein said detector circuit includes an operational amplifier having inverting and non-inverting inputs, said sensor coil being connected to both said inputs.

10. The detector of claim 9 wherein said predetermined value is less than 10 microamperes.

11. The sensor of claim 7 further including an electronic detector circuit having an output signal when said sensor coil detects unbalanced current between said conductors in excess of a predetermined value.

12. The detector of claim 11 wherein said detector circuit includes an operational amplifier having inverting and non-inverting inputs, said sensor coil being connected to both said inputs.

13. The detector of claim 12 wherein said predetermined value is less than 10 microamperes.

14. The detector of claim 13 wherein said output signal is an electrical output signal.

* * * * *